United States Patent
Tetzlaff et al.

(10) Patent No.: US 7,118,570 B2
(45) Date of Patent: *Oct. 10, 2006

(54) VESSEL SEALING FORCEPS WITH DISPOSABLE ELECTRODES

(75) Inventors: Philip M. Tetzlaff, Superior, CO (US); James S. Cunningham, Boulder, CO (US); Michael C. Moses, Boulder, CO (US); Roger F. Smith, Boulder, CO (US); Kristin D. Johnson, Louisville, CO (US); Paul R. Romero, Loveland, CO (US)

(73) Assignee: Sherwood Services AG, Schaffhausen (CH)

( * ) Notice: Subject to any disclaimer, the term of this patent is extended or adjusted under 35 U.S.C. 154(b) by 212 days.

This patent is subject to a terminal disclaimer.

(21) Appl. No.: 10/474,227

(22) PCT Filed: Apr. 6, 2001

(86) PCT No.: PCT/US01/11218

§ 371 (c)(1),
(2), (4) Date: Oct. 3, 2003

(87) PCT Pub. No.: WO02/080793

PCT Pub. Date: Oct. 17, 2002

(65) Prior Publication Data

US 2004/0236325 A1    Nov. 25, 2004

Related U.S. Application Data

(63) Continuation-in-part of application No. 09/425,696, filed on Oct. 22, 1999, now Pat. No. 6,511,480.

(51) Int. Cl.
*A61B 18/04* (2006.01)

(52) U.S. Cl. .............................. 606/48; 606/49; 606/51; 606/52

(58) Field of Classification Search ................. 606/41, 606/45, 48, 49–52, 174, 205–207
See application file for complete search history.

(56) References Cited

U.S. PATENT DOCUMENTS

| 371,664 A | 10/1887 | Brannan et al. |
| 702,472 A | 6/1902 | Pignolet |
| 728,883 A | 5/1903 | Downes |
| 1,586,645 A | 6/1926 | Bierman |

(Continued)

FOREIGN PATENT DOCUMENTS

| CA | 2104423 | 2/1994 |

(Continued)

OTHER PUBLICATIONS

PCT/US01/11340, International Search Report.

(Continued)

*Primary Examiner*—Rosiland Rollins

(57) ABSTRACT

A removable electrode assembly for use in combination with a forcep having opposing end effectors and a handle for effecting movement of the end effectors relative to one another. The electrode assembly includes a housing which is removably engageable with the forceps and a pair of electrodes which are attachable to a distal end of the housing. The electrodes are removably engageable with the end effectors of the forceps such that the electrodes reside in opposing relation relative to one another. The electrode assembly also includes a cover plate which is removably attachable to the housing and at least one stop member (439) for controlling the distance between the opposing electrodes. The stop member is selectively engageable with the electrodes.

11 Claims, 12 Drawing Sheets

U.S. PATENT DOCUMENTS

| | | |
|---|---|---|
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 4,005,714 A | 2/1977 | Hiltebrandt |
| 4,074,718 A | 2/1978 | Morrison, Jr. |
| 4,088,134 A | 5/1978 | Mazzariello |
| 4,165,746 A | 8/1979 | Burgin |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,558,672 A | 9/1996 | Edwards et al. |
| 5,562,699 A | 10/1996 | Heimberger et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,582,611 A | 12/1996 | Tsukagoshi et al. |
| 5,585,896 A | 12/1996 | Yamazaki et al. |
| 5,590,570 A | 1/1997 | LeMaire, III et al. |
| 5,603,711 A | 2/1997 | Parins et al. |
| 5,603,723 A | 2/1997 | Aranyi et al. |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,674,526 A | 9/1997 | Levin |
| 5,674,200 A | 10/1997 | Ruschke et al. |

| | | | | | | |
|---|---|---|---|---|---|---|
| 5,681,282 | A | 10/1997 | Eggers et al. | 6,110,171 A | 8/2000 | Rydell |
| 5,693,051 | A | 12/1997 | Schulze et al. | 6,113,596 A | 9/2000 | Hooven et al. |
| 5,695,522 | A | 12/1997 | LeMaire, III et al. | 6,113,598 A | 9/2000 | Baker |
| 5,700,261 | A | 12/1997 | Brinkerhoff | 6,117,158 A | 9/2000 | Measamer et al. |
| 5,702,390 | A | 12/1997 | Austin et al. | H1904 H | 10/2000 | Yates et al. |
| 5,707,369 | A | 1/1998 | Vaitekunas et al. | 6,126,658 A | 10/2000 | Baker |
| 5,709,680 | A | 1/1998 | Yates et al. | 6,152,923 A | 11/2000 | Ryan |
| 5,716,366 | A | 2/1998 | Yates | 6,174,309 B1 | 1/2001 | Wrublewski et al. |
| 5,727,428 | A | 3/1998 | LeMaire, III et al. | 6,179,834 B1 | 1/2001 | Buysse et al. |
| 5,735,848 | A | 4/1998 | Yates et al. | 6,179,837 B1 | 1/2001 | Hooven |
| 5,743,906 | A | 4/1998 | Parins et al. | 6,183,467 B1 | 2/2001 | Shapeton et al. |
| 5,755,717 | A | 5/1998 | Yates et al. | 6,187,003 B1 | 2/2001 | Buysse et al. |
| 5,766,130 | A | 6/1998 | Selmonosky | 6,190,386 B1 | 2/2001 | Rydell |
| 5,766,166 | A | 6/1998 | Hooven | 6,193,718 B1 | 2/2001 | Kortenbach et al. |
| 5,766,170 | A | 6/1998 | Eggers | 6,206,876 B1 | 3/2001 | Levine et al. |
| 5,769,849 | A | 6/1998 | Eggers | 6,206,877 B1 | 3/2001 | Kese et al. |
| 5,776,128 | A | 7/1998 | Eggers | 6,224,593 B1 | 5/2001 | Ryan et al. |
| 5,776,130 | A | 7/1998 | Buysse et al. | 6,228,080 B1 | 5/2001 | Gines |
| 5,779,701 | A | 7/1998 | McBrayer et al. | 6,228,083 B1 | 5/2001 | Lands et al. |
| 5,792,137 | A | 8/1998 | Carr et al. | 6,267,761 B1 | 7/2001 | Ryan |
| 5,792,177 | A | 8/1998 | Kaseda | 6,270,497 B1 | 8/2001 | Sekino et al. |
| 5,797,938 | A | 8/1998 | Paraschac et al. | 6,270,508 B1 | 8/2001 | Klieman et al. |
| 5,797,958 | A | 8/1998 | Yoon | 6,273,887 B1 | 8/2001 | Yamauchi et al. |
| 5,800,449 | A | 9/1998 | Wales | 6,277,117 B1 | 8/2001 | Tetzlaff et al. |
| 5,810,808 | A | 9/1998 | Eggers | 6,280,458 B1 | 8/2001 | Boche et al. |
| 5,810,811 | A | 9/1998 | Yates et al. | 6,283,961 B1 | 9/2001 | Underwood et al. |
| 5,810,877 | A | 9/1998 | Roth et al. | D449,886 S | 10/2001 | Tetzlaff et al. |
| 5,814,043 | A | 9/1998 | Shapeton | 6,322,561 B1 | 11/2001 | Eggers et al. |
| 5,820,630 | A | 10/1998 | Lind | 6,334,860 B1 | 1/2002 | Dorn |
| 5,827,271 | A | 10/1998 | Buysse et al. | 6,334,861 B1 | 1/2002 | Chandler et al. |
| 5,827,279 | A | 10/1998 | Hughett et al. | 6,350,264 B1 | 2/2002 | Hooven |
| 5,827,281 | A | 10/1998 | Levin | 6,352,536 B1 | 3/2002 | Buysse et al. |
| 5,833,690 | A | 11/1998 | Yates et al. | D457,958 S | 5/2002 | Dycus et al. |
| 5,843,080 | A | 12/1998 | Fleenor et al. | D457,959 S | 5/2002 | Tetzlaff et al. |
| 5,849,022 | A | 12/1998 | Sakashita et al. | 6,398,779 B1 | 6/2002 | Buysse et al. |
| 5,853,412 | A | 12/1998 | Mayenberger | 6,402,747 B1 | 6/2002 | Lindemann et al. |
| 5,876,401 | A | 3/1999 | Schulze et al. | 6,409,728 B1 | 6/2002 | Ehr et al. |
| 5,891,141 | A | 4/1999 | Rydell | H2037 H | 7/2002 | Yates et al. |
| 5,891,142 | A | 4/1999 | Eggers et al. | 6,419,675 B1 | 7/2002 | Gallo, Sr. |
| 5,893,863 | A | 4/1999 | Yoon | 6,425,896 B1 | 7/2002 | Baltschun et al. |
| 5,893,875 | A | 4/1999 | O'Connor et al. | 6,443,970 B1 | 9/2002 | Schulze et al. |
| 5,893,877 | A | 4/1999 | Gampp, Jr. et al. | 6,451,018 B1 | 9/2002 | Lands et al. |
| 5,902,301 | A | 5/1999 | Olig | 6,458,128 B1 | 10/2002 | Schulze |
| 5,906,630 | A | 5/1999 | Anderhub et al. | 6,458,130 B1 | 10/2002 | Frazier et al. |
| 5,908,420 | A | 6/1999 | Parins et al. | 6,464,704 B1 | 10/2002 | Schmaltz et al. |
| 5,913,874 | A | 6/1999 | Berns et al. | 6,503,248 B1 | 1/2003 | Levine |
| 5,921,984 | A | 7/1999 | Sutcu et al. | 6,506,189 B1 | 1/2003 | Rittman, III et al. |
| 5,935,126 | A | 8/1999 | Riza | 6,511,480 B1 | 1/2003 | Tetzlaff et al. |
| 5,944,718 | A | 8/1999 | Daffon et al. | 6,514,251 B1 | 2/2003 | Ni et al. |
| 5,951,549 | A | 9/1999 | Richardson et al. | 6,544,264 B1 | 4/2003 | Levine et al. |
| 5,954,720 | A | 9/1999 | Wilson et al. | 6,569,162 B1 | 5/2003 | He |
| 5,976,132 | A | 11/1999 | Morris | 6,585,735 B1 | 7/2003 | Frazier et al. |
| 5,989,277 | A | 11/1999 | LeMaire, III et al. | 6,620,161 B1 | 9/2003 | Schulze et al. |
| 6,004,335 | A | 12/1999 | Vaitekunas et al. | 6,682,528 B1 | 1/2004 | Frazier et al. |
| 6,010,516 | A | 1/2000 | Hulka et al. | 6,685,724 B1 | 2/2004 | Haluck |
| 6,024,741 | A | 2/2000 | Williamson et al. | 6,733,498 B1 | 5/2004 | Paton et al. |
| 6,024,744 | A | 2/2000 | Kese et al. | 6,743,229 B1 | 6/2004 | Buysse et al. |
| 6,033,399 | A | 3/2000 | Gines | D496,997 S | 10/2004 | Dycus et al. |
| 6,039,733 | A | 3/2000 | Buysse et al. | D499,181 S | 11/2004 | Dycus et al. |
| 6,041,679 | A | 3/2000 | Slater et al. | 6,926,716 B1 | 8/2005 | Baker et al. |
| 6,050,996 | A | 4/2000 | Schmaltz et al. | 6,929,644 B1 | 8/2005 | Truckai et al. |
| 6,053,914 | A | 4/2000 | Eggers et al. | 2002/0107517 A1 | 8/2002 | Witt et al. |
| 6,053,933 | A | 4/2000 | Balazs et al. | 2002/0188294 A1 | 12/2002 | Couture et al. |
| D424,694 | S | 5/2000 | Tetzlaff et al. | 2003/0018331 A1 | 1/2003 | Dycus et al. |
| D425,201 | S | 5/2000 | Tetzlaff et al. | 2003/0069571 A1 | 4/2003 | Treat et al. |
| RE36,795 | E | 7/2000 | Rydell | 2003/0078578 A1 | 4/2003 | Truckai Csaba et al. |
| 6,083,223 | A | 7/2000 | Baker | 2003/0139741 A1 | 7/2003 | Goble et al. |
| 6,086,586 | A | 7/2000 | Hooven | 2003/0139742 A1 | 7/2003 | Wampler et al. |
| 6,090,107 | A | 7/2000 | Borgmeier et al. | 2003/0158549 A1 | 8/2003 | Swanson |
| 6,096,031 | A | 8/2000 | Mitchell et al. | 2003/0199869 A1 | 10/2003 | Johnson et al. |
| 6,096,037 | A | 8/2000 | Mulier et al. | 2004/0147925 A1 | 7/2004 | Buysse et al. |
| 6,099,550 | A | 8/2000 | Yoon | 2004/0225288 A1 | 11/2004 | Buysse et al. |
| 6,102,909 | A | 8/2000 | Chen et al. | 2004/0236325 A1 | 11/2004 | Tetzlaff et al. |

| | | | |
|---|---|---|---|
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0101951 A1 | 5/2005 | Wham et al. |
| 2005/0113818 A1 | 5/2005 | Sartor et al. |

FOREIGN PATENT DOCUMENTS

| | | |
|---|---|---|
| DE | 2415263 | 10/1975 |
| DE | 29616210 | 1/1997 |
| DE | 19608716 | 4/1997 |
| DE | 19751108 | 5/1999 |
| EP | 0364216 A1 | 4/1990 |
| EP | 0518230 A1 | 12/1992 |
| EP | 0 541 930 B1 | 5/1993 |
| EP | 0572131 | 12/1993 |
| EP | 0572131 A1 | 12/1993 |
| EP | 0584787 A1 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0853922 A1 | 7/1998 |
| EP | 0887046 A3 | 1/1999 |
| EP | 0923907 A1 | 6/1999 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| GB | 2214430 A | 6/1989 |
| JP | 501068 | 9/1984 |
| JP | 502328 | 3/1992 |
| JP | 5-40112 | 2/1993 |
| JP | 06343644 A2 | 12/1994 |
| JP | 07265328 A2 | 10/1995 |
| JP | 07285328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 10/1973 |
| SU | 401367 | 11/1974 |
| WO | WO 92/06642 | 4/1992 |
| WO | WO 94/08524 A | 4/1994 |
| WO | WO 95/02369 | 1/1995 |
| WO | WO 95/07662 | 3/1995 |
| WO | WO 96/13218 | 9/1996 |
| WO | WO 97/00647 | 1/1997 |
| WO | WO 97/00648 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 A | 3/1999 |
| WO | WO 99/40857 | 8/1999 |
| WO | WO 99/51158 | 10/1999 |
| WO | WO 99/66850 A | 12/1999 |
| WO | WO 00/24330 | 5/2000 |
| WO | WO 00/24331 | 5/2000 |
| WO | WO 00/41638 | 7/2000 |
| WO | WO 00/53112 | 9/2000 |
| WO | WO 01/17448 A | 3/2001 |
| WO | WO 01/54604 | 8/2001 |
| WO | WO 01/54604 A1 | 8/2001 |
| WO | WO 02/07627 | 1/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 A1 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 04/032777 | 4/2004 |
| WO | WO 2004/052221 A1 | 6/2004 |
| WO | WO 04/073490 | 9/2004 |
| WO | WO 2004/082495 A1 | 9/2004 |
| WO | WO 2004/098383 A1 | 11/2004 |
| WO | WO 04/103156 | 12/2004 |

OTHER PUBLICATIONS

PCT/US01/11420, International Search Report.
PCT/US02/01890, International Search Report.
PCT/US02/11100, International Search Report.
PCT/US04/03436, International Search Report.
PCT/US04/13273, International Search Report.
PCT/US04/15311, International Search Report.
EP 98944778, International Search Report.
EP 98958575, International Search Report.
EP 04027479, International Search Report.
EP 04027705, International Search Report.
EP 04027314, International Search Report.
"Innovations in Electrosurgery" Sales/Product Literature.
LigaSure Vessel Sealing System, the Seal of Confidence in General, Gynecologic, Urologic, and Laparaoscopic Surgery Sales/Product Literture.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC.
"Reducing Needlestick Injuries in the Operating Room" Sales/Product Literature.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, July/Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations That Work, Mar. 2000.

Muller et al., "Extended Left Hemicolectomy Using the LigaSure Vessel Sealing System" Innovations That Work, Sep. 1999.

Herman et al., "Laparoscopic Intestinal Resection With the LigaSure Vessel Sealing Sytem: A Case Report" Innovations That Work, Feb. 2002.

Carus et al., "Initial Experience With The LigaSure Vessel Sealing System in Abdominal Surgery" Innovations That Work, Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing For Hemostasis During Gynecologic Surgery" Sales Product Literature.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olsson et al, "Radical Cystectomy in Females" Current Surgical Techniques in Urology, vol. 14, Issue 3.

E. David Crawford "Use of a Novel Vessel Sealing Technology In Management of the Dorsal Velnous Complex" Sales Product Literature.

Jarrett et al., "Use of the LigaSure Vessel System for Peri-Hilar Vessels in Laparoscopic Nephrectomy" Sales Product Literature.

E. David Crawford "Evaluation of a New Vessel Sealing Device in Urologic Cancer Surgery" Sales Product Literature.

Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.

Dulemba et al. "Use of a Bipolar Electrothermal Vessel Sealer in Laparoscopically Assisted Vaginal Hysterectomy" Sales Product Literature.

Johnson et al. "Evaluation of a Bipolar electrothermal Vessel Sealing Device in Hemorrholdectomy" Sales Product Literature.

Sigel et al. "The Mechanism of Blood Vessel Closure by High Frequency Electrocoagulation" Surgery Gynecology & Obstetrics, Oct. 1965 pp. 823-831.

Bergdahl et al. "Studies on Caogulation and the Development of an Automatic Computerized Bipolar Coagulator" J.Neurosurg, vol. 75, Jul. 1991, pp. 148-151.

Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System In Hemorrhoidectormy" American College Of Surgeons (ACS) Clinicla Congress Poster (2000).

Sayfan et al. "Sutureless Closed Hemorrhoidectomy: A New Technique" Annals Of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hermostasis During Pelvic Surgery" Int'l Federation Of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) Wold Congress.

Crawford et al. "Use of the LigaSure Vessel Sealin System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemonthoidectomy" British Journal of Surgery 2002, 89, 154-157.

Int'l Search Report PCT/US01/11218.

Int'l Search Report PCT/US99/24869.

Int'l Search Report PCT/US98/18640.

Int'l Search Report PCT/US98/23950.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.

Olsson et al. "Radical Cystectomy in Females" Current Surgical Techniques in Urology, vol. 14, Issue 3, 2001.

Dulemba et al. "Use of a Bipolar Electrothermal Vessel Sealer in Laparoscopically Assisted Vaginal Hysterectomy" Sales Product Literature; Jan. 2004.

Johnson et al. "Evaluation of a Bipolar electrothermal Vessel Sealing Device in Hemorrhoidectomy" Sales Product Literature; Jan., 2004.

International Search Report PCT/US01/11224 dated Nov. 13, 2001.

International Search Report EP 98958575.7 dated Sep. 20, 2002.

International Search Report EP 04013772 dated Apr. 1, 2005.

International Search Report EP 05013895 dated Oct. 14, 2005.

International Search Report EP 05017281 dated Nov. 16, 2005.

US 6,090,109, 07/2000, Lands et al. (withdrawn)

US 6,663,629, 12/2003, Buysse et al. (withdrawn)

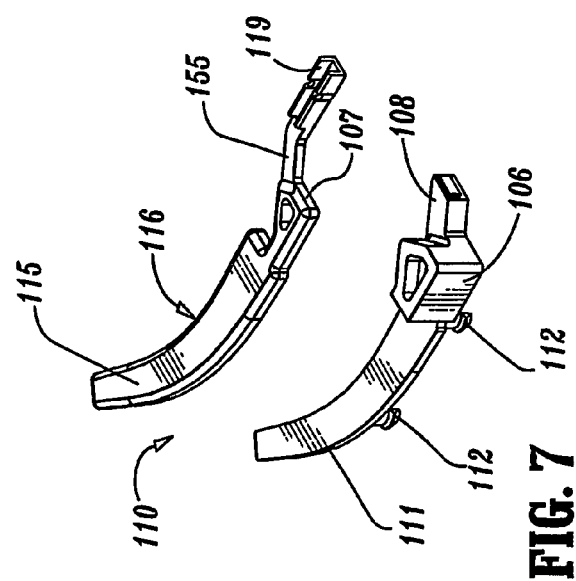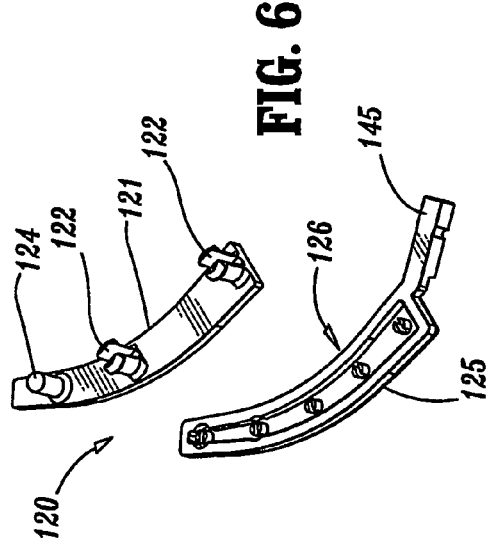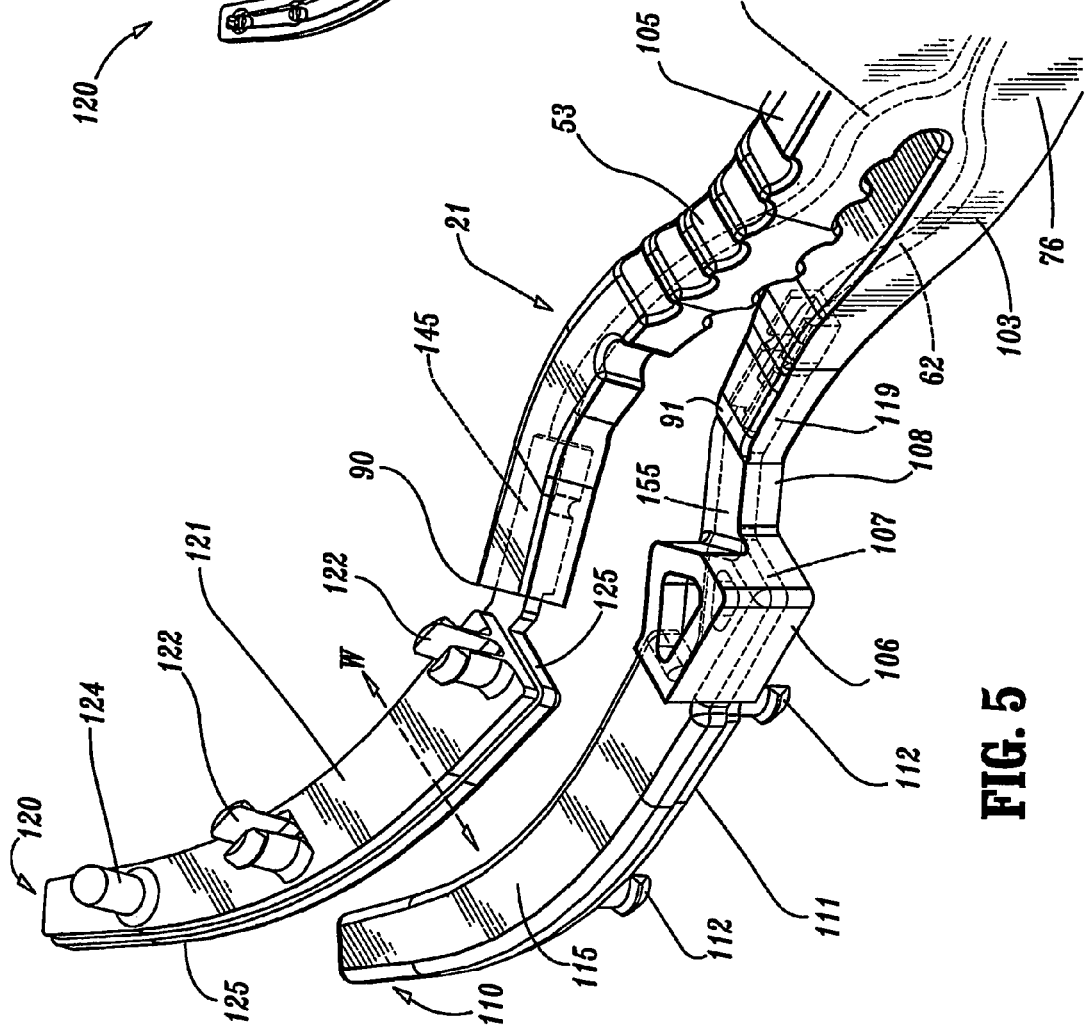

VESSEL SEALING FORCEPS WITH DISPOSABLE ELECTRODES

CROSS REFERENCE TO RELATED APPLICATIONS

This application is a continuation-in-part of U.S. application Ser. No. 09/425,696 filed on Oct. 22, 1999 by Tetzlaff et al now U.S. Pat. No. 6,511,480, which claims priority to U.S. application Ser. No. 09/178,027 filed Oct. 23, 1998 now U.S. Pat. No. 6,277,117, by Tetzlaff et al, and U.S. application Ser. No. 09/177,950 filed Oct. 23, 1998 by Frazier et al., now Abandoned the entire contents of all of these applications are hereby incorporated by reference.

This application is a 371 of PCT US01/11218 filed Apr. 6, 2001.

BACKGROUND

The present disclosure relates to electrosurgical forceps used for open surgical procedures and/or laparoscopic surgical procedures. More particularly, the present disclosure relates to a bipolar forceps having a disposable electrode assembly for sealing, cauterizing, coagulating/desiccating and/or cutting vessels and vascular tissue.

TECHNICAL FIELD

A hemostat or forceps is a simple plier-like tool which uses mechanical action between its jaws to constrict tissue and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize, cut and/or seal tissue.

By utilizing an electrosurgical forceps, a surgeon can either cauterize, coagulate/desiccate and/or cut tissue and/or simply reduce or slow bleeding, by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of end effectors and which are both electrically coupled to an electrosurgical generator. Each electrode is charged to a different electric potential. Since tissue is a conductor of electrical energy, when the effectors are utilized to clamp or grasp tissue therebetween, the electrical energy can be selectively transferred through the tissue.

The process of coagulating small vessels is fundamentally different than vessel sealing. For the purposes herein the term coagulation is defined as a process of desiccating tissue wherein the tissue cells are ruptured and dried. Vessel sealing is defined as the process of liquefying the collagen in the tissue so that it cross-links and reforms into a fused mass. Thus, coagulation of small vessels is sufficient to close them, however, larger vessels need to be sealed to assure permanent closure.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. In some instances a fused vessel wall is optimum between 0.001 and 0.006 inches. Below this range, the seal may shred or tear and above this range the lumens may not be properly or effectively sealed.

Numerous bipolar electrosurgical forceps have been proposed in the past for various open surgical procedures. However, some of these designs may not provide uniformly reproducible pressure to the blood vessel and may result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cutting and/or sealing vessels or tissue. However, some of these designs may not provide uniformly reproducible pressure to the blood vessel and may result in an ineffective or non-uniform seal.

Many of these instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

It has also been found that cleaning and sterilizing many of the prior art bipolar instruments is often impractical as electrodes and/or insulation can be damaged. More particularly, it is known that electrically insulative materials, such as plastics, can be damaged or compromised by repeated sterilization cycles.

Thus, a need exists to develop a bipolar forceps which can seal vessels and tissue consistently and effectively and which will not be damaged by continued use and cleaning.

SUMMARY

The present disclosure relates to a removable electrode assembly for use with a forceps having opposing end effectors and a handle for effecting relative movement of the end effectors with respect to one another. The electrode assembly includes a cover plate having at least one portion which is removably engageable with at least a portion of the forceps and an electrode housing having at least one portion which is removably engageable with at least a portion of the forceps. A pair of electrodes attaches to a distal end of the housing. Preferably, the electrodes are removably engageable with the end effectors of the forceps such that the electrodes are disposed in opposing relation to one another. The instrument also includes at least one stop member which controls the distance between the opposing electrodes. Preferably, the stop members being selectively engageable with the electrodes. The electrode assembly can be employed with both open surgical procedures as well as laparoscopic surgical procedures.

In one embodiment, the electrodes include an electrically conductive sealing surface and an insulating substrate and the stop member is removably attached to the insulating substrate. Preferably, the insulating substrate of each of the electrodes includes at least one mechanical interface, e.g., detent, for engaging a complimentary mechanical interface, e.g., notch, disposed on the corresponding end effector of the forceps.

In another embodiment, the substrate includes at least one detent and the mechanical interface of the corresponding end effector includes at least one complimentary key-like socket for slideably and securely receiving the detent.

In yet another embodiment, the stop member is attached to at least one of the electrodes by thermal spraying and protrudes about 0.001 inches to about 0.005 inches from the inner facing surface of the jaw member. Preferably, the stop member protrudes about 0.002 inches to about 0.003 inches from the inner facing surface of the jaw member.

Another embodiment of the present disclosure relates to a bipolar electrosurgical instrument which includes a forceps having opposing end effectors and a handle for effecting relative movement of the end effectors with respect to one another and an electrode assembly which is removably attached to the forceps. The electrode assembly includes a pair of opposing electrodes attached to a distal end thereof which are removably engageable with one of the end effectors such that the electrodes reside in opposing relation to one another. At least one stop member which is selectively engageable with the electrodes controls the distance between the opposing electrodes.

BRIEF DESCRIPTION OF THE DRAWINGS

Various embodiments of the subject instrument are described herein with reference to the drawings wherein:

FIG. 5 is an enlarged, perspective view of a distal end of the disposable electrode assembly of FIG. 4;

FIG. 6 is a perspective view with parts separated of an upper electrode of the disposable electrode assembly of FIG. 5;

FIG. 7 is a perspective view with parts separated of a lower electrode of the disposable electrode assembly of FIG. 5;

DETAILED DESCRIPTION

Figure 1:
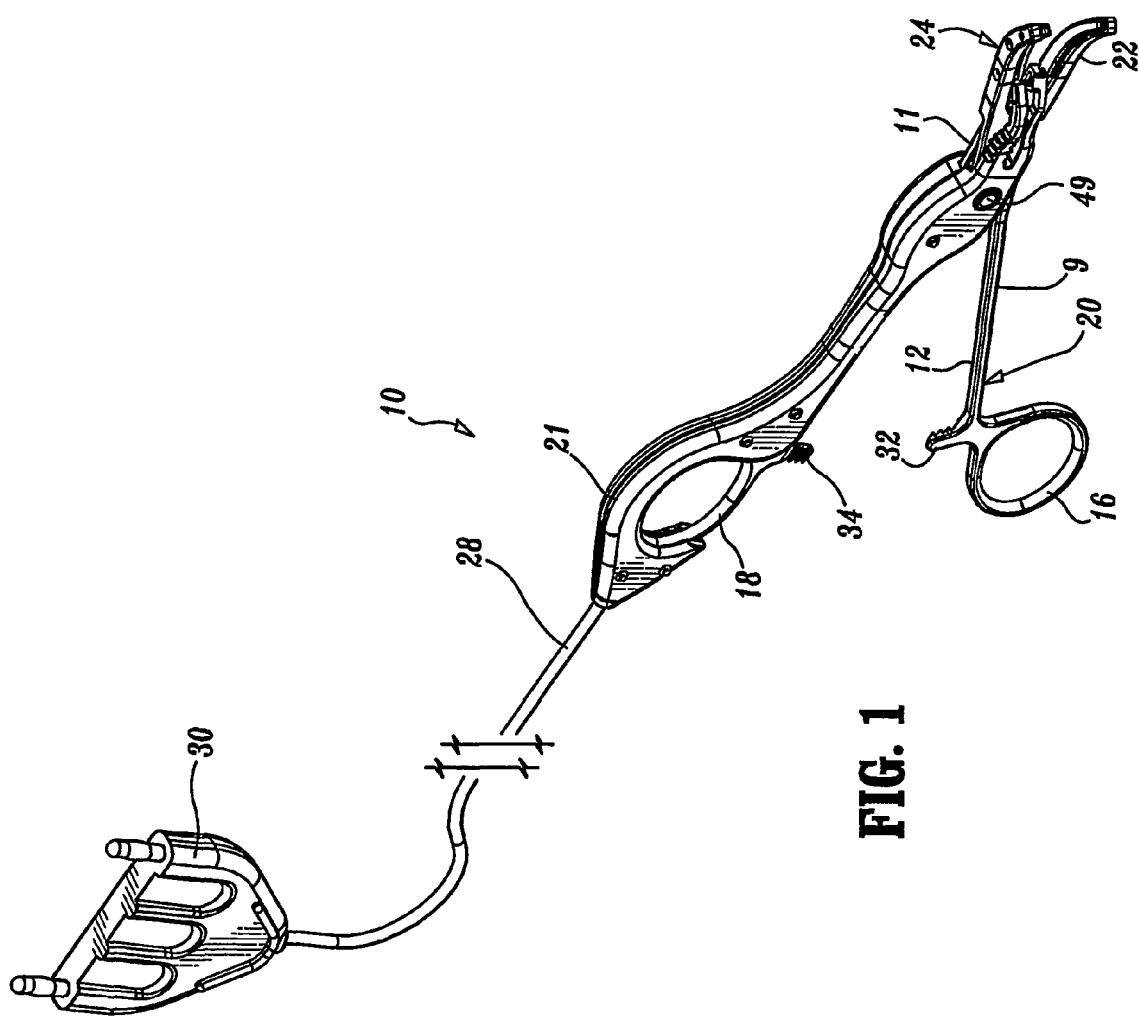
FIG. 1 is a perspective view of a bipolar forceps according to the present disclosure.
Figure 2:
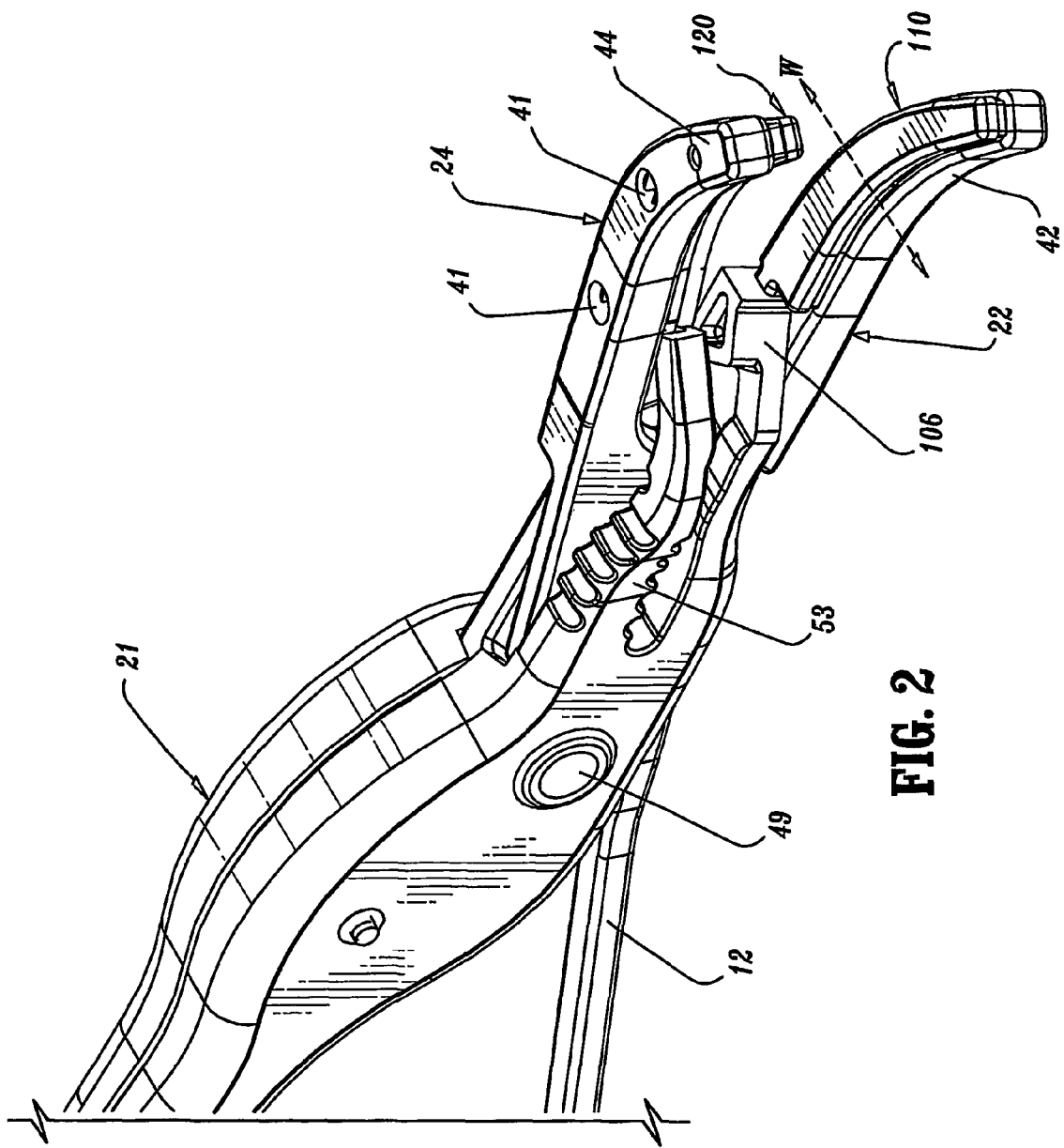
FIG. 2 is an enlarged, perspective view of a distal end of the bipolar forceps shown in FIG. 1.
Figure 3:
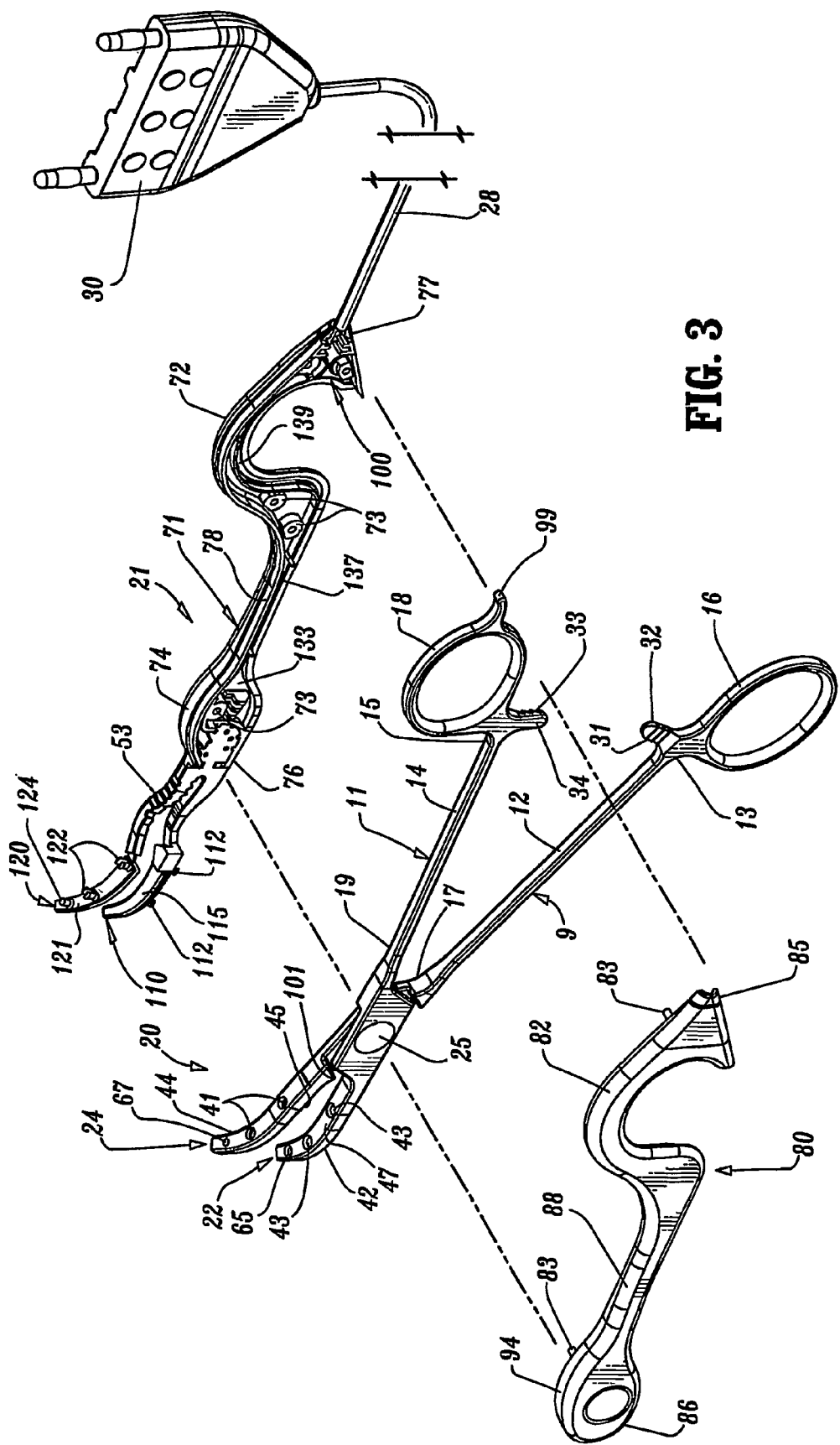
FIG. 3 is a perspective view with parts separated of the forceps shown in FIG. 1.

Referring now to FIGS. 1–3, a bipolar forceps 10 for use with open and/or laparoscopic surgical procedures includes a mechanical forceps 20 and an electrode assembly 21. In the drawings and in the description which follows, the term "proximal", as is traditional, will refer to the end of the forceps 10 which is closer to the user, while the term "distal" will refer to the end which is further from the user.

Mechanical forceps 20 includes first and second members 9 and 11 which each have an elongated shaft 12 and 14, respectively. Shafts 12 and 14 each include a proximal end 13 and 15 and a distal end 17 and 19, respectively. Each proximal end 13, 15 of each shaft portion 12, 14 includes a handle member 16 and 18 attached thereto to allow a user to effect movement of at least one of the shaft portions 12 and 14 relative to one another. Extending from the distal end 17 and 19 of each shaft portion 12 and 14 are end effectors 22 and 24, respectively. The end effectors 22 and 24 are movable relative to one another in response to movement of handle members 16 and 18.

Figure 8:
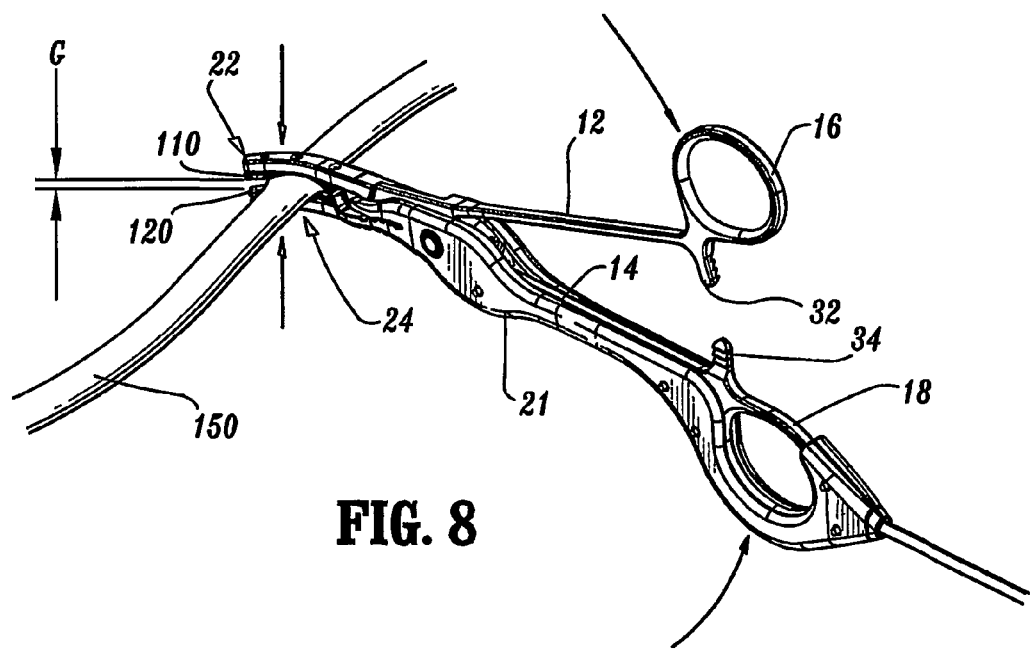
FIG. 8 is a perspective view of the forceps of the present disclosure showing the operative motion of the forceps to effect sealing of a tubular vessel.

Preferably, shaft portions 12 and 14 are affixed to one another at a point proximate the end effectors 22 and 24 about a pivot 25 such that movement of the handles 16 and 18 impart movement of the end effectors 22 and 24 from an open position wherein the end effectors 22 and 24 are disposed in spaced relation relative to one another to a clamping or closed position wherein the end effectors 22 and 24 cooperate to grasp a tubular vessel 150 therebetween (see FIG. 8). It is envisioned that pivot 25 has a large surface area to resist twisting and movement of forceps 10 during operation. Clearly, the forceps 10 can be designed such that movement of one or both of the handles 16 and 18 will only cause one of the end effectors, e.g., 22, to move with respect to the other end effector, e.g., 24.

As best seen in FIG. 3, end effector 24 includes an upper or first jaw member 44 which has an inner facing surface 45 and a plurality of mechanical interfaces disposed thereon which are dimensioned to releasable engage a portion of a disposable electrode assembly 21 which will be described in greater detail below. Preferably, the mechanical interfaces include sockets 41 which are disposed at least partially through inner facing surface 45 of jaw member 44 and which are dimensioned to receive a complimentary detent attached to upper electrode 120 of the disposable electrode assembly 21. While the term socket is used herein, it is contemplated that either a male or female mechanical interface may be used on jaw member 44 with a mating mechanical interface disposed on the disposable electrode assembly 21.

In some cases, it may be preferable to manufacture mechanical interfaces 41 along another side of jaw member 44 to engage a complimentary mechanical interface of the disposable electrode assembly 21 in a different manner, e.g., from the side. Jaw member 44 also includes an aperture 67 disposed at least partially through inner face 45 of end effector 24 which is dimensioned to receive a complimentary guide pin 124 disposed on electrode 120 of the disposable electrode assembly 21.

End effector 22 includes a second or lower jaw member 42 which has an inner facing surface 47 which opposes inner facing surface 45. Preferably, jaw members 45 and 47 are dimensioned generally symmetrically, however, in some cases it may be preferable to manufacture the two jaw members 42 and 44 asymmetrically depending upon a particular purpose. In much the same fashion as described above with respect to jaw member 44, jaw member 42 also includes a plurality of mechanical interfaces or sockets 43 disposed thereon which are dimensioned to releasable engage a complimentary portion disposed on an electrode 110 of the disposable electrode assembly 21 as described below. Likewise, jaw member 42 also includes an aperture 65 disposed at least partially through inner face 47 which is dimensioned to receive a complimentary guide pin 126 (see FIG. 4) disposed on electrode 110 of the disposable electrode assembly 21.

Preferably, shaft members 12 and 14 of the mechanical forceps 20 are designed to transmit a particular desired force to the opposing inner facing surfaces 47 and 45 of the of the jaw members 22 and 24, respectively, when clamped. In particular, since the shaft members 12 and 14 effectively act together in a spring-like manner (i.e., bending that behaves like a spring), the length, width, height and deflection of the shaft members 12 and 14 will directly effect the overall transmitted force imposed on opposing jaw members 42 and 44. Preferably, jaw members 22 and 24 are more rigid than the shaft members 12 and 14 and the strain energy stored in the shaft members 12 and 14 provides a constant closure force between the jaw members 42 and 44.

Each shaft member 12 and 14 also includes a ratchet portion 32 and 34. Preferably, each ratchet, e.g., 32, extends from the proximal end 13 of its respective shaft member 12 towards the other ratchet 34 in a generally vertically aligned manner such that the inner facing surfaces of each ratchet 32 and 34 abut one another when the end effectors 22 and 24 are moved from the open position to the closed position. Each ratchet 32 and 34 includes a plurality of flanges 31 and 33, respectively, which project from the inner facing surface of each ratchet 32 and 34 such that the ratchets 32 and 34 can interlock in at least one position. In the embodiment shown in FIG. 1, the ratchets 32 and 34 interlock at several different positions. Preferably, each ratchet position holds a specific, i.e., constant, strain energy in the shaft members 12 and 14 which, in turn, transmit a specific force to the end effectors 22 and 24 and, thus, the electrodes 120 and 110. A design without a ratchet system or similar system would require the user to hold the jaw members 42 and 44 together by applying constant force to the handles 16 and 18 which may yield inconsistent results.

In some cases it may be preferable to include other mechanisms to control and/or limit the movement of the jaw members 42 and 44 relative to one another. For example, a ratchet and pawl system could be utilized to segment the movement of the two handles into discrete units which will, in turn, impart discrete movement to the jaw members 42 and 44 relative to one another.

Preferably, at least one of the shaft members, e.g., 14, includes a tang 99 which facilitates manipulation of the forceps 20 during surgical conditions as well as facilitates attachment of electrode assembly 21 on mechanical forceps 20 as will be described in greater detail below.

As best seen in FIGS. 2, 3 and 5, disposable electrode assembly 21 is designed to work in combination with mechanical forceps 20. Preferably, electrode assembly 21 includes housing 71 which has a proximal end 77, a distal end 76 and an elongated shaft plate 78 disposed therebetween. A handle plate 72 is disposed near the proximal end 77 of housing 71 and is sufficiently dimensioned to releasably engage and/or encompass handle 18 of mechanical forceps 20. Likewise, shaft plate 78 is dimensioned to encompass and/or releasably engage shaft 14 and pivot plate 74 disposed near the distal end 76 of housing 71 is dimensioned to encompass pivot 25 and at least a portion of distal end 19 of mechanical forceps 20. It is contemplated that the electrode assembly 21 can be manufactured to engage either the first or second members 9 and 11 of the mechanical forceps 20 and their respective component parts 12, 16 or 14, 18, respectively.

In the embodiment shown in FIG. 2, handle 18, shaft 14, pivot 25 and a portion of distal end 19 are all dimensioned to fit into corresponding channels located in housing 71. For example, a channel 139 is dimensioned to receive handle 18, a channel 137 is dimensioned to receive shaft 14 and a channel 133 is dimensioned to receive pivot 25 and a portion of distal end 19.

Electrode assembly 21 also includes a cover plate 80 which is also designed to encompass and/or engage mechanical forceps 20 in a similar manner as described with respect to the housing 71. More particularly, cover plate 80 includes a proximal end 85, a distal end 86 and an elongated shaft plate 88 disposed therebetween. A handle plate 82 is disposed near the proximal end 85 and is preferably dimensioned to releasable engage and/or encompass handle 18 of mechanical forceps 20. Likewise, shaft plate 88 is dimensioned to encompass and/or releasable engage shaft 14 and a pivot plate 94 disposed near distal end 86 is designed to encompass pivot 25 and distal end 19 of mechanical forceps 20. Preferably, handle 18, shaft 14, pivot 25 and distal end 19 are all dimensioned to fit into corresponding channels (not shown) located in cover plate 80 in a similar manner as described above with respect to the housing 71.

Figure 4:
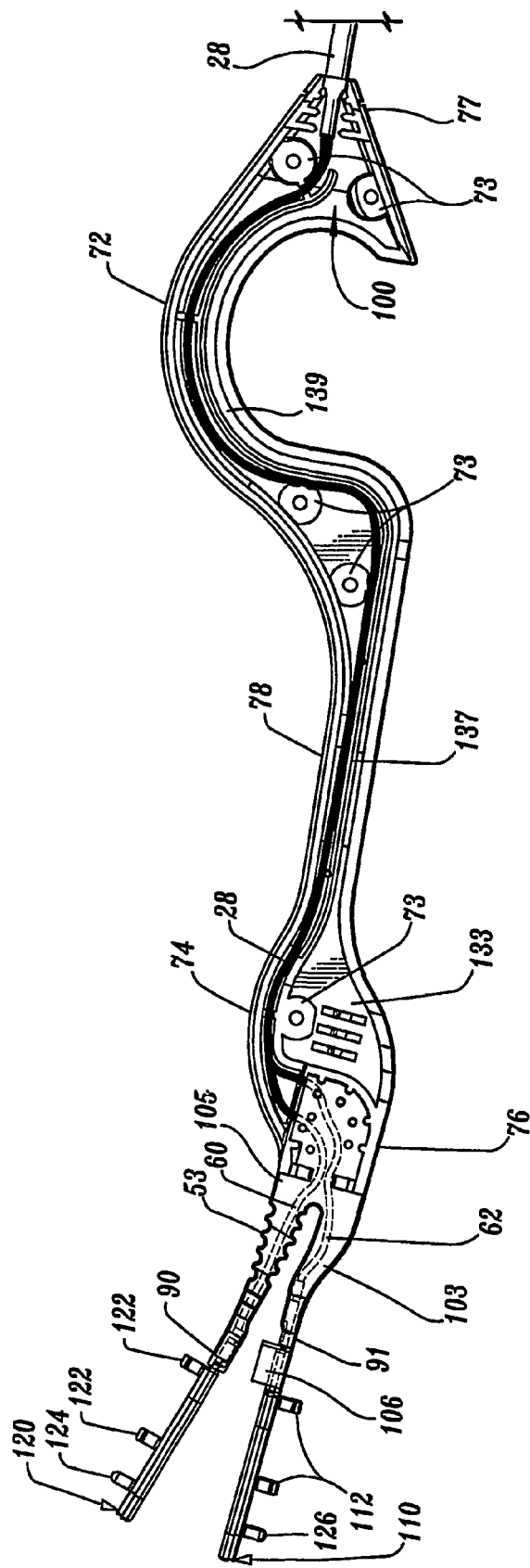
FIG. 4 is an enlarged, side view of a disposable electrode assembly of FIG. 1 shown without a cover plate.

As best seen with respect to FIGS. 3 and 4, housing 71 and cover plate 80 are designed to engage one another over first member 11 of mechanical forceps 20 such that first member 11 and its respective component parts, e.g., handle 18, shaft 14, distal end 19 and pivot 25, are disposed therebetween. Preferably, housing 71 and cover plate 80 include a plurality of mechanical interfaces disposed at various positions along the interior of housing 71 and cover plate 80 to effect mechanical engagement with one another. More particularly, a plurality of sockets 73 are disposed proximate handle plate 72, shaft plate 78 and pivot plate 74 of housing 71 and are dimensioned to releasably engage a corresponding plurality of detents 83 extending from cover plate 80. It is envisioned that either male or female mechanical interfaces or a combination of mechanical interfaces may be disposed within housing 71 with mating mechanical interfaces disposed on or within cover plate 80.

As best seen with respect to FIGS. 5–7, the distal end 76 of electrode assembly 21 is bifurcated such that two prong-like members 103 and 105 extend outwardly therefrom to support an electrode 110 and 120, respectively. More particularly, electrode 120 is affixed at an end 90 of prong 105 and electrode 110 is affixed at an end 91 of prong 103. It is envisioned that the electrodes 110 and 120 can be affixed to the ends 91 and 90 in any known manner such as, e.g., frictional or snap-fit engagement.

A pair of wires 60 and 62 are connected to the electrodes 120 and 110, respectively, as best seen in FIGS. 4 and 5. Preferably, wires 60 and 62 are bundled together and form a wire bundle 28 which runs from a terminal connector 30 (see FIG. 3), to the proximal end 77 of housing 71, along the interior of housing 71, to distal end 76. Wire bundle 28 is separated into wires 60 and 62 proximate distal end 76 and the wires 60 and 62 are connected to each electrode 120 and 110, respectively. In some cases it may be preferable to capture the wires 60 and 62 or the wire bundle 28 at various pinch points along the inner cavity of the electrode assembly 21 and enclosing the wires 60 and 62 within electrode assembly 21 by attaching the cover plate 80.

This arrangement of wires 60 and 62 is designed to be convenient to the user so that there is little interference with the manipulation of bipolar forceps 10. As mentioned above, the proximal end of the wire bundle 28 is connected to a terminal connector 30, however, in some cases it may be preferable to extend wires 60 and 62 to an electrosurgical generator (not shown). Alternatively, wires 60 and 62 can remain separated and extend along the first and second members 9 and 11.

As best seen in FIG. 6, electrode 120 includes an electrically conductive seal surface 126 and an electrically insulative substrate 121 which are attached to one another by snap-fit engagement or some other method of assembly, e.g., substrate 121 is overmolded to capture the electrically conductive seal surface 126. Preferably, substrate 121 is made from an injection molded plastic material and is shaped to mechanically engage a corresponding socket 41 located in jaw member 44 of end effector 24. The substrate 121 not only insulates the electric current but it also aligns electrode 120 both of which contribute to the seal quality and consistency. For example, by overmolding the conductive surface 126 to the substrate 121, the alignment and thickness of the electrode 120 can be controlled.

Preferably, substrate 121 includes a plurality of bifurcated detents 122 which are shaped to compress during insertion into sockets 41 and expand and releasably engage sockets 41 after insertion. It is envisioned that snap-fit engagement of the electrode 120 and the jaw member 44 will accommodate a broader range of manufacturing tolerances. Substrate 121 also includes an alignment or guide pin 124 which is dimensioned to engage aperture 67 of jaw member 44.

Conductive seal surface 126 includes an wire crimp 145 designed to engage the distal end 90 of prong 105 of electrode assembly 21 and electrically engage a corresponding wire connector affixed to wire 60 located within electrode assembly. Seal surface 126 also includes an opposing face 125 which is designed to conduct an electrosurgical current to a tubular vessel or tissue 150 when it is held thereagainst.

Electrode 110 includes similar elements for insulating and conducting electrosurgical current to tissue 150. More particularly, electrode 110 includes an electrically conductive seal surface 116 and an electrically insulative substrate 111 which are attached to one another by snap-fit engagement or some other method of assembly. Substrate 111 includes a plurality of bifurcated detents 112 and an alignment pin 126 (see FIG. 4) which are dimensioned to engage a corresponding plurality of sockets 43 and aperture 65 located in jaw member 42. Conductive seal surface 116 includes an extension 155 having a wire crimp 119 which engages the distal end 91 of prong 103 and electrically engages a corresponding wire connector affixed to wire 62 located in housing 71. Seal surface 116 also includes an opposing face 115 which conducts an electrosurgical current to a tubular vessel or tissue 150 when it is held thereagainst. Alternatively, electrodes 110 and/or 120 can be formed as one piece and include similar components for insulating and conducting electrical energy.

As best seen in FIG. 7, substrate 111 also includes an extension 108 and a stop member 106 which is designed to engage corresponding extension 155 and an interface 107 located on conductive seal 116. To assemble electrode 110, stop member 106 and extension 108 are overmolded onto interface 107 and extension 155 of conductive seal 116. After assembly, wire crimp 119 is then inserted into end 91 of prong member 103 and connected to wire 62.

It is known that as the tissue is compressed and electrosurgical energy is applied to the tissue, the impedance of the tissue decreases as the moisture level decreases. As a result, two mechanical factors play an important role in determining seal thickness and effectiveness, i.e., the pressure applied between opposing faces 47 and 45 and the gap distance between the opposing electrodes 110 and 120 (see FIG. 5). Jaw members 42 and 44 are configured to provide for the opposing electrodes 110 and 120 to be in a desired gap range (e.g., 0.001 and 0.006 inches) at the end of the tissue sealing process (See FIG. 8). The material conditions and components relating to the assembly of the electrode assembly 21 and the mechanical forceps 20 are configured to fall within specific manufacturing tolerances to assure that the gap between electrodes will not vary outside the desired range.

It is also known that tissue thickness is very difficult to control by force alone, i.e., too much force and the two poles would touch and the little energy would travel through the tissue resulting in a bad seal or too little force and the seal would be too thick. Applying the correct force is important for other reasons: to oppose the vessel lumens; reduce the tissue impedance to a low enough value that allows enough current through the tissue; and to overcome the forces of expansion during tissue heating in addition to contributing towards creating the required end tissue thickness which is an indication of a good seal.

It is also known that the size of the gap effects the tissue seal. For example, if a gap is too great, i.e., the jaws do not compress the tissue enough, the tissue does not properly liquefy the collagen for effective sealing. If, on the other hand, the gap is too small, i.e., the jaws compress the tissue too much, the electrosurgical energy effectively severs the tissue which is also undesirous. It has been found that in order to effectively seal tissue and overcome the shortcomings described above, the gap distance (range) 151 (See FIG. 8) between the opposing electrodes 110 and 120 is preferably between about 0.001 inches to about 0.006 inches and more preferably, between about 0.002 inches to about 0.005 inches.

In order to assure that the desired gap range is achieved after assembly and that the correct force is applied to seal the tissue, substrate 111 includes at least one stop member, 106, which is designed to restrict and/or regulate movement of the two electrodes 110 and 120 relative to one another. Preferably, forceps 20 also includes at least one stop member, e.g., 101 (see FIG. 3), for restricting and/or regulating the distance between end effectors 22 and 24 and/or the closure force applied between opposing inner facing surfaces 47 and 45 of end effectors 22 and 24 which will, in turn, regulate the distance between electrodes 110 and 120. Since stop 106 is part of the disposable electrode assembly 21, this stop has the added benefit of being dependent on the material of the disposable electrode assembly 21. Preferably, a "step" stop is utilized due to its ease of manufacture and simplicity.

It is contemplated that the stop member can be positioned at various points along the disposable electrode assembly to achieve the aforedescribed desired gap range and/or the stop member can be positioned on other parts of the instrument, e.g., handles 16, 18, jaws 42, 44, and/or shafts 12, 14.

Preferably, the seal surfaces 115 and 125 are relatively flat to avoid current concentrations at sharp edges and to avoid arcing between high points. In addition and due to the reaction force of the tissue 150 when engaged, jaw members 42 and 44 are preferably manufactured to resist bending. For example and as best seen in FIG. 3, the jaw members 42 and 44 and the corresponding electrodes 110 and 120 are preferably tapered along width "W" which is advantageous for two reasons: 1) the taper will apply constant pressure for a constant tissue thickness at parallel; 2) the thicker proximal portion of the electrode, e.g., 110, will resist bending due to the reaction force of the tissue 150. The tapered shape of the electrode, e.g., 110, is determined by calculating the mechanical advantage variation from the distal to proximal end of the electrode 110 and adjusting the width of the electrode 110 accordingly.

Preferably, at least one of the prong members, e.g., 105, is resilient or includes a flex relief portion 53 which permits movement of the two prong members 105 and 103 and, thus, the two electrodes 120 and 110, relative to one another. As seen best in FIG. 3, the electrode assembly 21 is removably attached to the mechanical forceps 20 by initially moving prong 105 towards prong 103 by bending prong 105 at flex relief portion 53. The electrodes 110 and 120 are then slid between opposing jaw members 42 and 44 in their open position such that detents 112 and 122 and guide pins 126 and 124, respectively, are each disposed in alignment with each corresponding socket 43 and 41 or aperture 65 and 67, respectively. Housing 71 is also positioned accordingly such that shaft 14, handle 18 and pivot 25 are all positioned proximate their corresponding channels 137, 139 and 133 located within housing 71.

When flex relief portion 53 is released, each electrode 110 and 120 is engaged with jaw member 42 and 44, respectively, i.e., detents 112, 122 engage sockets 43, 41, and housing 71 is engaged with mechanical forceps 20. The cover plate 80 is then attached to housing 71 in the manner described above. The bipolar forceps 10 is now ready for operation.

In one embodiment, the electrode assembly 21 is attached to the mechanical forceps 20 in a different manner: For example and as best Illustrated in FIG. 3, the electrode assembly 21 can be engaged with the mechanical forceps 20 in the following four-step manner: 1) electrode assembly 21 and cover plate 80 are pivoted backward such that tang 99 engages a slot 100 in electrode assembly 21; 2) electrode assembly 21 and cover plate 80 are then pivoted forward to engage shaft 14 of mechanical forceps 20 therebetween; 3) detents 112 of electrode 110 are then engaged with sockets 43 of jaw member 22; and 4) detents 122 of electrode 120 are engaged with sockets 41 of jaw member 24.

Figure 16A:
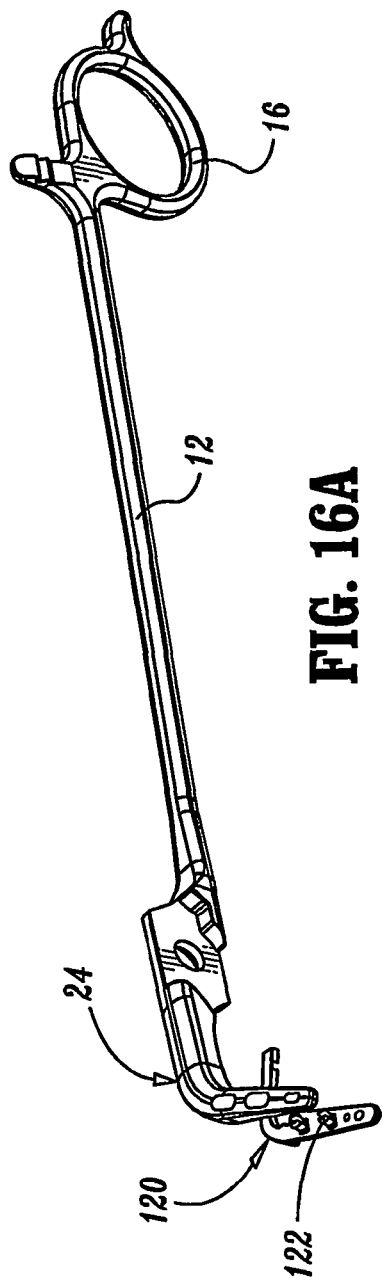
FIGS. 16A–16B show various views of another embodiment of the electrode assembly according to the present disclosure wherein the electrode assembly engages the forceps in a slide-like manner.
Figure 16B:
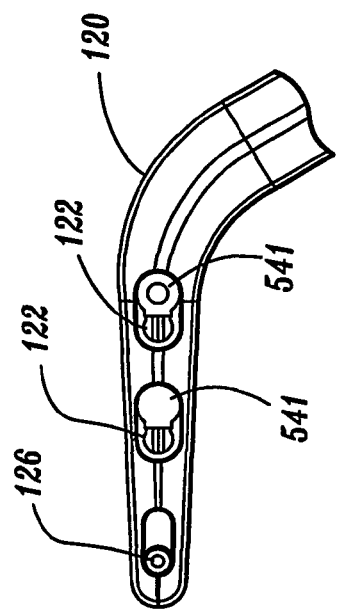

In another embodiment as shown in FIGS. 16A–16B, the electrode assembly 21 engages the forceps 20 by way of a slide-on assembly technique. More particularly, the slide-on version includes a series of keyhole-like apertures 541 disposed in the end effectors 22 and 24 which slidingly engage the corresponding mechanical interfaces 112, 122 and 124 extending from the insulators 111 and 121, respectively. It is envisioned that the slide-on attachment feature facilitates removal and replacement of the electrode assembly 21 and reduces manufacturing costs by minimizing the critical tolerances of the detents 112, 122 and alignment pins 126.

Further, it is contemplated that a slide-on assembly method compared to a snap-on assembly method may improve reliability of the forceps 20 due to less plastic deformation at assembly. For example, the snap-on technique requires deformation of the fork-like detents 112, 122 to promote secure engagement of the electrode assembly 21 with the end effectors 22 and 24. As can be appreciated, the less aggressive, slide-on technique reduces material deformation during assembly which, in turn, may lengthen the overall life of the instrument, prevent slippage of the electrode assembly 21 and prevent separation of the electrode assembly 21 during activation.

Further, it is contemplated that even though the slide-on assembly technique may engage the electrode assembly 21 in a less aggressive manner during assembly, the uniquely-designed key-like interface 541, once engaged, provides a more aggressive connection which contributes to better "seating" of the electrode assembly 21 within the end effectors 22 and 24. Again, the more aggressive seating of the electrode assembly 21 prevents slippage of the electrode assembly 21 and prevents separation of the electrode assembly 21 during activation.

Figure 9:
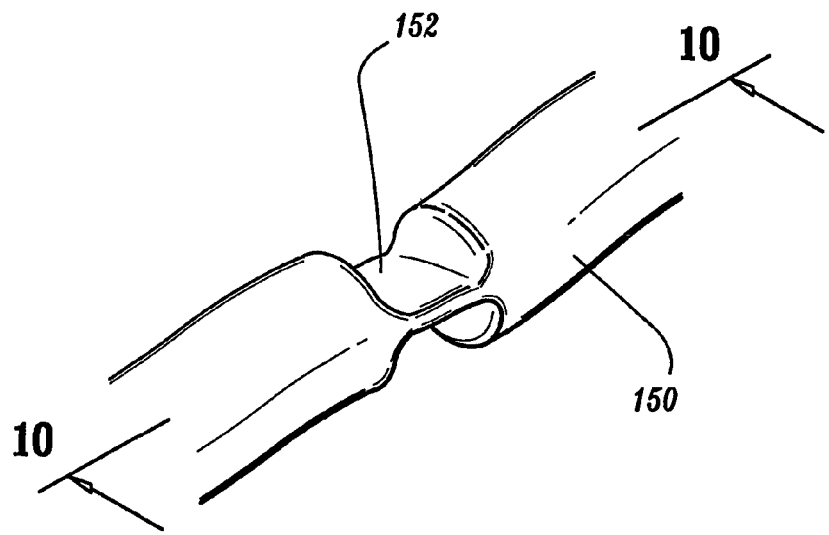
FIG. 9 is an enlarged, partial perspective view of a sealing site of a tubular vessel.
Figure 10:
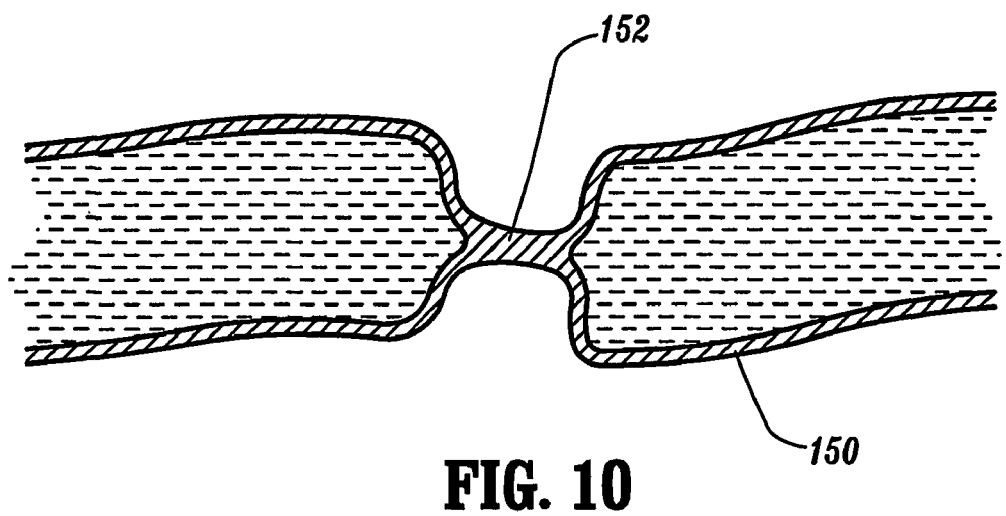
FIG. 10 is a longitudinal cross-section of the sealing site taken along line 10—10 of FIG. 9.
Figure 11:
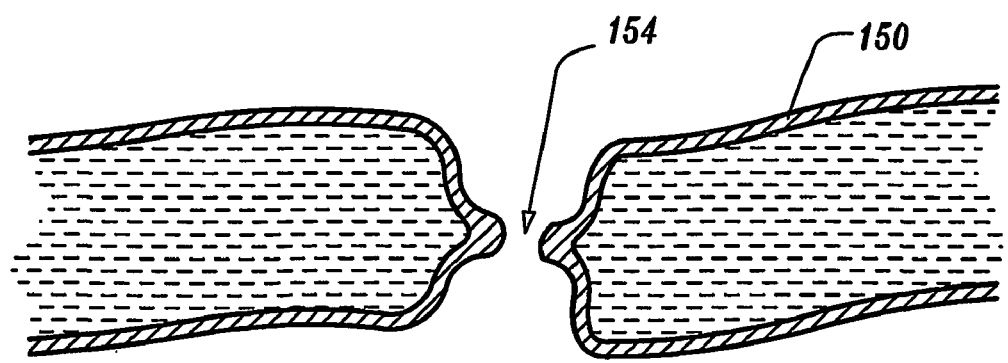
FIG. 11 is a longitudinal cross-section of the sealing site of FIG. 9 after separation of the tubular vessel.

FIG. 8 shows the bipolar forceps 10 during use wherein the handle members 16 and 18 are moved closer to one another to apply clamping force to the tubular tissue 150 to effect a seal 152 as shown in FIGS. 9 and 10. Once sealed, the tubular vessel 150 can be cut along seal 152 to separate the tissue 150 and form gap 154 therebetween as shown in FIG. 11.

After the bipolar forceps 10 is used or if the electrode assembly 21 is damaged, the electrode assembly 21 can be easily removed and/or replaced by reversing the above attachment procedure and a new electrode assembly 21 can be engaged with the mechanical forceps 20 in the same manner. For example, the electrode assembly 21 can be disengaged from the mechanical forceps 20 in the following four-step manner: 1) the detents 122 of electrode 120 are disengaged from the sockets 41 of jaw member 24; 2) the detents 112 of electrode 110 are disengaged from the sockets 43 of jaw member 22; 3) the electrode assembly 21 and cover plate 80 are disengaged from shaft 14 of mechanical forceps 20; and 4) the electrode assembly 21 and cover plate 80 are pivoted such that tang 99 disengages from slot 100 in electrode assembly 21.

It is envisioned that by making the electrode assembly 21 disposable, the electrode assembly 21 is less likely to become damaged since it is only intended for a single use and, therefore, does not require cleaning or sterilization. As a result, the functionality and consistency of the vital sealing components, e.g., the conductive surface 126, 116 and insulating surface 121, 111 will assure a uniform and quality seal.

Figure 12:
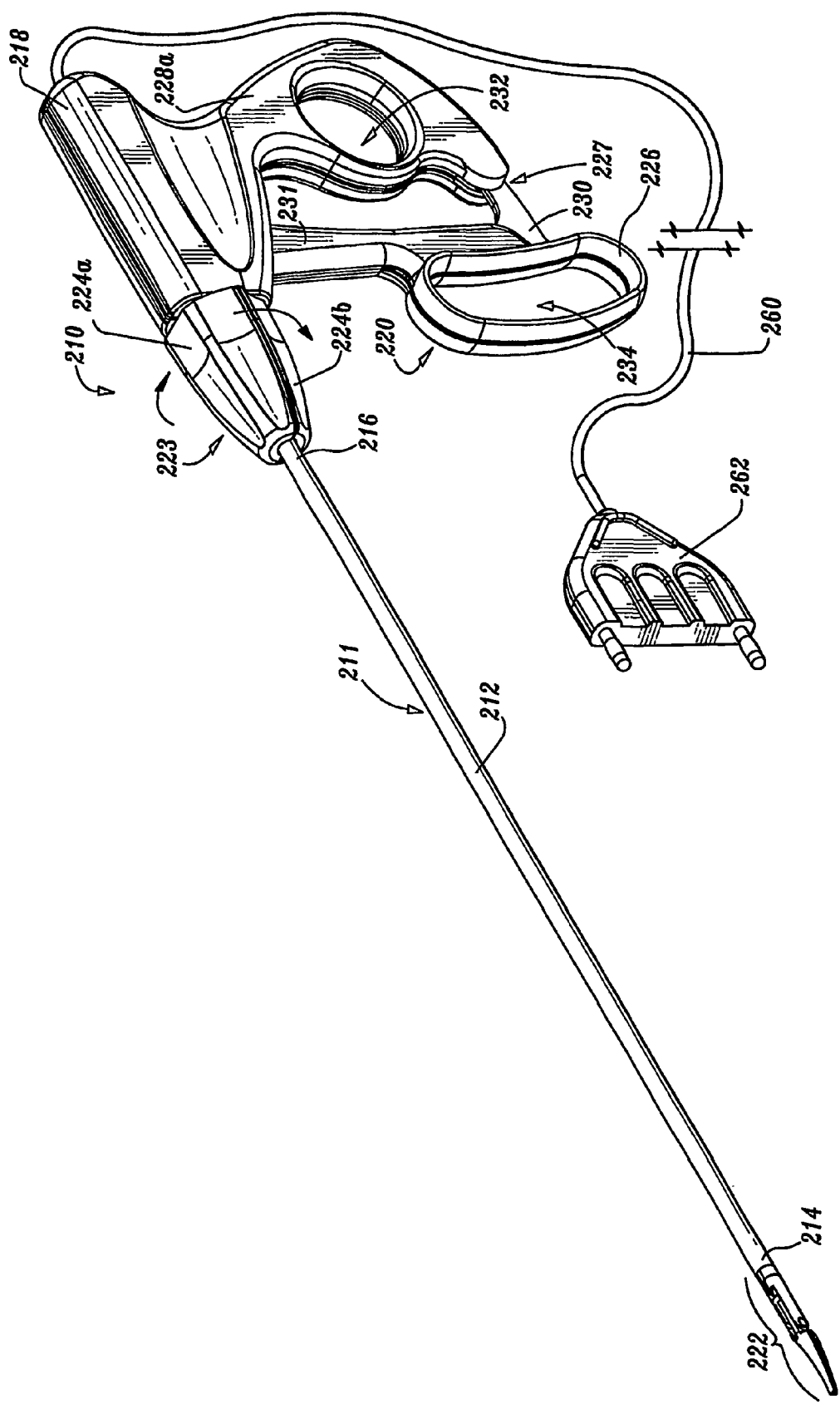
FIG. 12 is a perspective view of another embodiment of the present disclosure.
Figure 13:
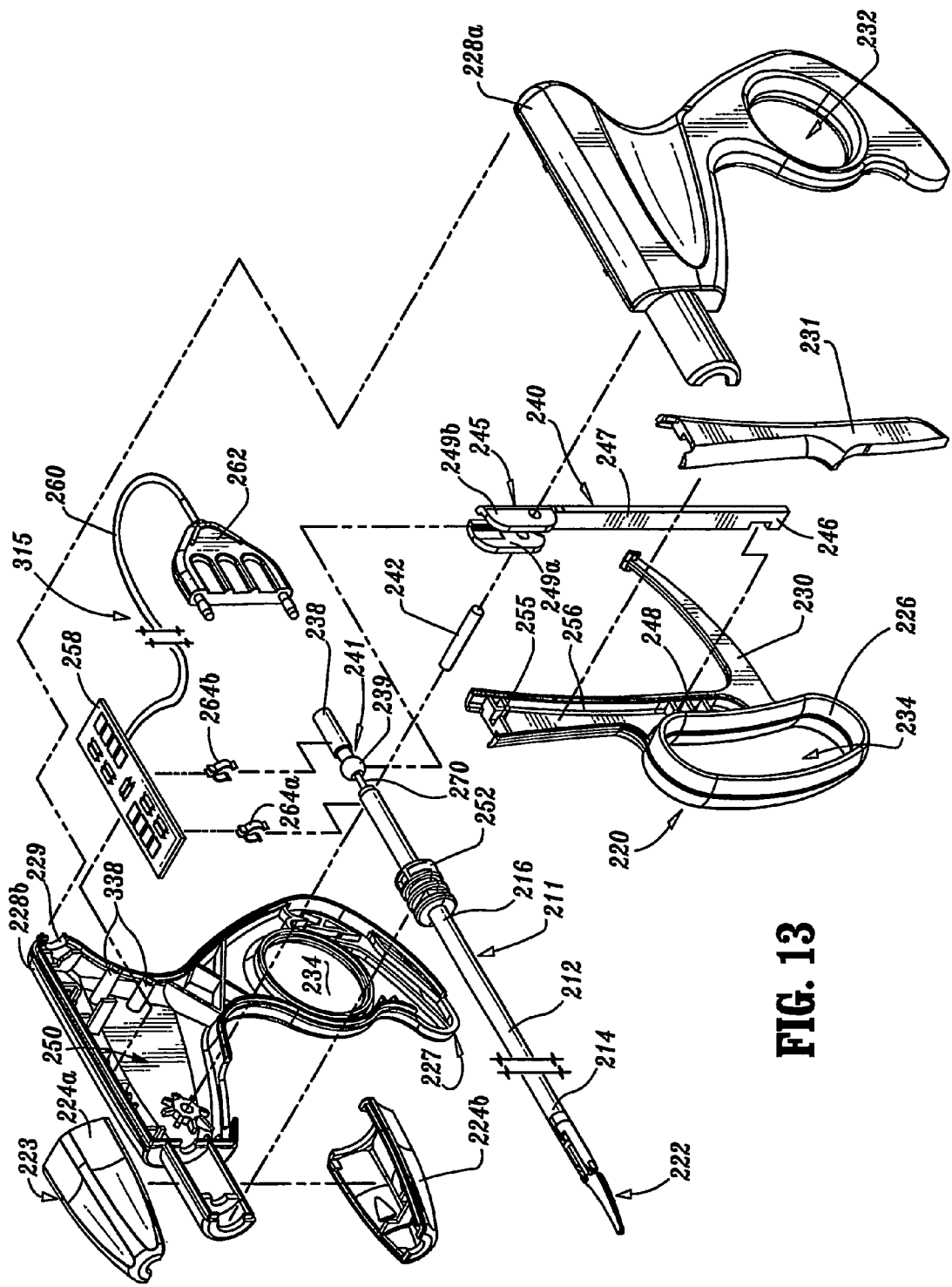
FIG. 13 is an exploded view of the embodiment of FIG. 12.
Figure 14:
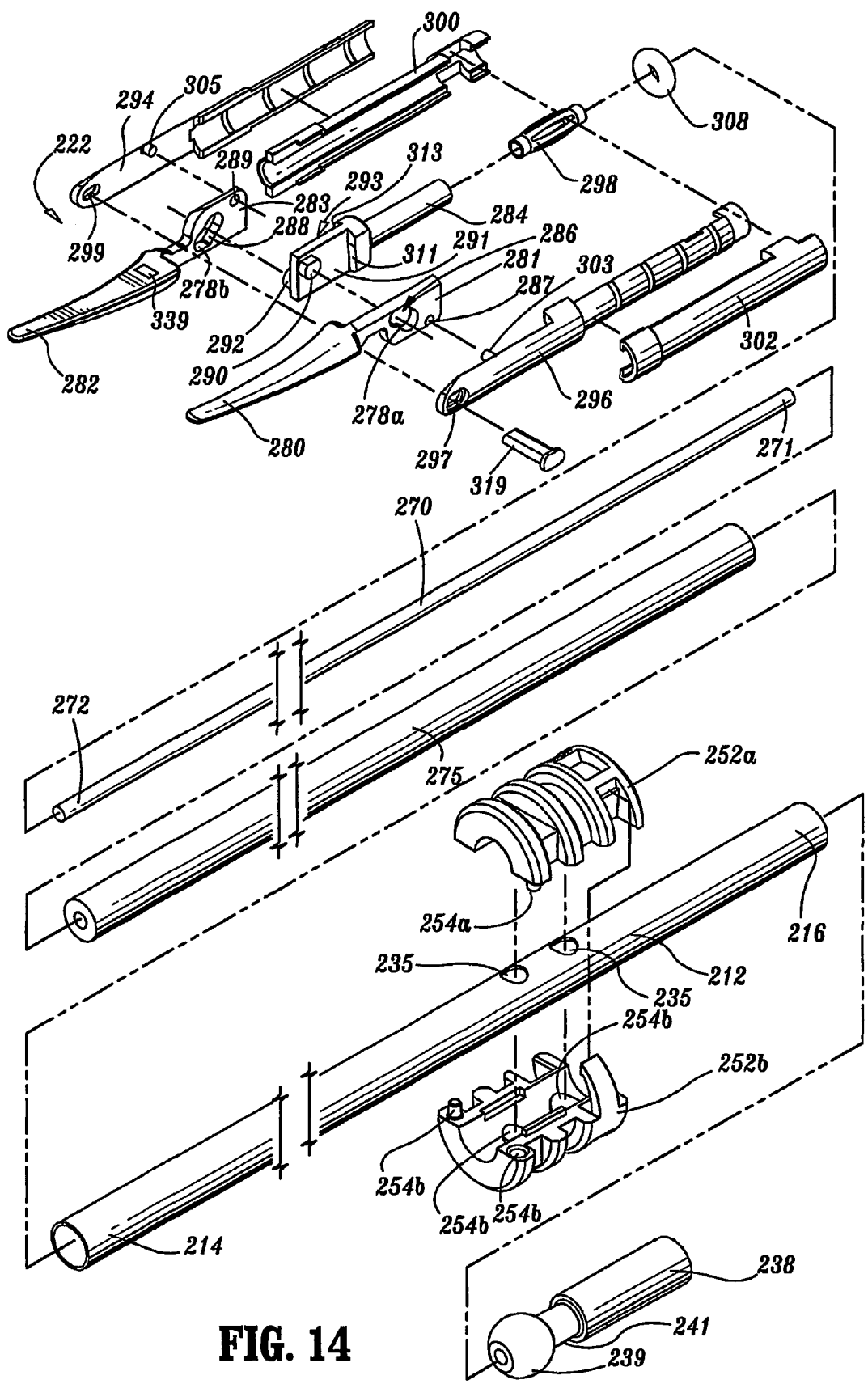
FIG. 14 is an enlarged exploded view of a working end of the embodiment of FIGS. 12 and 13.

FIGS. 12–14 show another embodiment of the present disclosure for use with endoscopic surgical procedures and includes a bipolar forceps 210 having a drive rod assembly 211 coupled to a handle assembly 218. The drive rod assembly 211 includes an elongated hollow shaft portion 212 having a proximal end 216 and a distal end 214. An end effector assembly 222 is attached to the distal end 214 of shaft 212 and includes a pair of opposing jaw members 280 and 282. Preferably, handle assembly 218 is attached to the proximal end 216 of shaft 212 and includes an activator 220 for imparting movement of the jaw members 280 and 282 from an open position wherein the jaw members 280 and 282 are disposed in spaced relation relative to one another, to a clamping or closed position wherein the jaw members 280 and 282 cooperate to grasp tissue 150 therebetween.

As best seen in FIG. 13, activator 220 includes a movable handle 226 having an aperture 234 defined therein for receiving at least one of the operator's fingers and a fixed handle 228 having an aperture 232 defined therein for receiving an operator's thumb. Movable handle 226 is selectively moveable from a first position relative to fixed handle 228 to a second position in closer proximity to the fixed handle 228 to close jaw members 280 and 282. Preferably, fixed handle 228 includes a channel 227 which extends proximally for receiving a ratchet 230 which is coupled to movable handle 226. This structure allows for progressive closure of end effector assembly 222 as well as locking engagement of opposing jaw members 280 and 282. In some cases it may be preferable to include other mechanisms to control and/or limit the movement of handle 226 relative to handle 228 such as, e.g., hydraulic, semi-hydraulic and/or gearing systems.

Fixed handle 228 includes a rotating assembly 223 for controlling the rotational movement of end effector assembly 222 about a longitudinal axis "A" of the elongated shaft 212. Preferably, rotating assembly 223 includes upper and lower knob portions 224a and 224b, respectively, which releasably engage one another about a gear 252 which is attached to shaft 212. A pair of handle sections 228a and 228b engage one another by way of a plurality of mechanical interfaces to form fixed handle 228. As best seen in FIG. 13, each handle section 228a and 228b is generally hollow such that a cavity 250 is formed therein for housing various internal components which make up the forceps 210. For example, cavity 250 houses a PC board 258 which controls the electrosurgical energy being transmitted from an electrosurgical generator (not shown) to each jaw member 280 and 282. More particularly, electrosurgical energy is generated from an electrosurgical generator and transmitted to the PC board by cable 260 which attached through a wire port 229 disposed in the proximal end of handle assembly 218. The PC board 258 converts the electrosurgical energy from the generator into two different electrical potentials which are transmitted to each jaw member 280 and 282 by a separate terminal clip 264b and 264a, respectively, which will be explained in more detail below with respect to FIG. 14.

Referring to FIG. 14, rod assembly 211 includes a drive rod 270 which has a proximal end 271 and a distal end 272. A piston 238 is attached to the proximal end 271 of drive rod 270 and includes a generally rounded head portion 239 and a notch 241 located between the head portion 239 and the proximal end of piston 238. Preferably, clevis flanges 249a and 249b of arm 240 are dimensioned to receive head 239 therebetween when arm 240 is assembled between handle sections 228a and 228b (see FIG. 6). Movement of the handle 226 towards fixed handle 228 imparts pivotal movement of the upper end 245 of arm 240 at a pivot point 255 which, in turn, imparts movement of the piston 238 from a first position wherein the piston 238 is disposed further from end effector assembly 222 to a second position wherein piston 238 is in closer proximity to end effector assembly 222. As explained in greater detail below, movement of the piston 238 between first and second positions imparts linear movement to drive rod 270 which, in turn, moves jaw members 280 and 282 toward and away from each other.

Seating the generally rounded head 239 between clevis flanges 249a and 249b enables the user to utilize the rotating assembly 223 effectively without interfering with the linear movement of the piston 238.

The end effector assembly 222 includes first jaw 280, second jaw 282 and an electrically insulating yoke 284 disposed therebetween. Preferably, jaw member 280 and jaw member 282 are movable from an open position to a closed position by movement of the handle assembly 218 as described above. It is contemplated that either both or one of the jaw members 280 and 282 can be movable relative to one another. First jaw member 280 has a first flange 281 which extends therefrom and a cam slot 86 located therethrough. Likewise, second jaw 282 has a second flange 283 which extends therefrom and a cam slot 288 located therethrough.

The end effector assembly 222 also includes an outer nose portion 294 and an inner nose portion 296 which engage jaw members 282 and 280, respectively. A first pivot 305 is located on outer nose portion 294 and is dimensioned to engage a corresponding pivot hole 289 located on flange 283. A second pivot 303 is located on inner nose portion 296 and is dimensioned to engage a corresponding pivot hole 287 located on flange 281. The center of rotation for first jaw member 280 is at a first pivot hole 287 and the center of rotation for second jaw member 282 is at a second pivot hole 289. Preferably, each nose portion 294 and 296 is made from an electrically conductive material and transmits electrosurgical energy to a respective jaw member 282 and 280 as described in more detail below.

As mentioned above with respect to FIG. 13, electrosurgical energy is transmitted from the electrosurgical generator to an connector assembly 315 which includes the PC board 258 which converts the energy into first and second poles. A pair of terminal clips 264a and 264b are connected to PC board 258 and transfer the first and second poles of alternating potential, respectively, to the drive rod assembly 211. Clip 264a connects to shaft 212 and conducts the first pole to jaw member 282 and clip 264b connects to piston 238 which is, in turn, connected to drive rod 270. The second pole is conducted along drive rod 270 to jaw member 280. Both the drive rod 270 and the shaft 212 are made from an electrically conductive material and preferably an insulation sleeve 275 is disposed between drive rod 270 and shaft 212 to prevent the forceps 210 from short circuiting.

As best seen in FIG. 14, the inner nose portion 296 is electrically connected with drive rod 270 and the outer nose portion 294 is electrically connected to shaft 212. The inner and outer nose portions 296 and 294 capture yoke 284 along with flanges 283 and 281. Yoke 284 moves axially along axis "A" in a space between inner and outer portions 296 and 294 and a spacer stake 319 maintains the separation of the nose portions 296 and 294 at their distal ends. Stake 319 is dimensioned to engage and lock the inner and outer nose portions 296 and 294 together, which, in turn locks jaw members 280 and 282 atop yoke 284. In some cases it may be preferable to dimension stake 319 such that stake 319 acts as a stop member and controls the gap distance between the opposing jaw members 280 and 282 relative to one another. In this case, stake 319 is formed from an electrically insulative material such as plastic. The nose portions 294 and 296 provide lateral support for the flanges 281 and 283 and help ensure that detents 290 and 292 remain within cam slots 286 and 288, respectively.

End effector assembly 222 also includes an inner insulator 302 and an outer insulator 300 for maintaining electrical insulation between poles. Outer insulator 300 insulates outer nose portion 294 from inner nose portion 296 and drive rod 270 which conduct the second pole of electrical energy. Inner insulator 302 insulates inner nose portion 296 from outer nose portion 294 and shaft 212 which conduct the first pole of electrical energy. In this manner, outer nose portion 294 can provide electrical continuity between shaft 212 and jaw member 282, while inner nose portion 296 can provide electrical continuity between drive rod 270 and jaw member 280.

Preferably, a spring contact 298 is utilized to maintain the electrical connection between drive rod 270 and inner nose portion 296 during axial motion of the drive rod 270. A donut-shaped spacer 308 can also be utilized to assure linear motion of the drive rod 270 within sleeve 275 and to prevent accidental short circuiting of the forceps 210.

Referring back to FIG. 14, yoke 284 is preferably formed from an electrically insulative material such as plastic. A first side 291 of yoke 284 faces first flange 281 and a second side 293 of yoke 284 faces second flange 283. When yoke 84 is positioned between flanges 281 and 283, yoke 284 electrically insulates first jaw member 80 from second jaw member 282. In this manner, bipolar electrosurgical current can be conducted through tissue 350 which is grasped between jaws 280 and 282 without flanges 281 and 283 short circuiting.

In order to achieve a desired gap range (e.g., about 0.001 to about 0.006 inches and, preferably, about 0.002 inches to about 0.003 inches) and apply a desired force to seal the tissue, at least one jaw member 280 and/or 282 includes a stop member 339 which limits the movement of the two opposing jaw members 280 and 282 relative to one another. As explained above, in some cases it may be preferable to dimension stake 319 such that it acts like a stop member and limits the movement of the two opposing jaw members 280 and 282 relative to one another. Preferably, stop member 339 and/or stake 319 is made from an insulative material and is dimensioned to limit opposing movement of the jaw members 280 and 282 to within the above gap range.

Figure 15A:
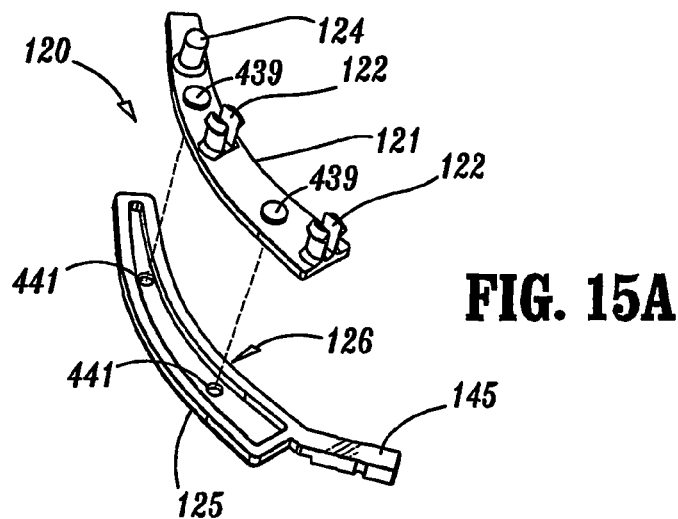
FIGS. 15A–15C show various views of another embodiment according to the present disclosure which shows stop members which are dimensioned as plugs to selectively attach to inner facing surfaces of the jaw members.
Figure 15B:
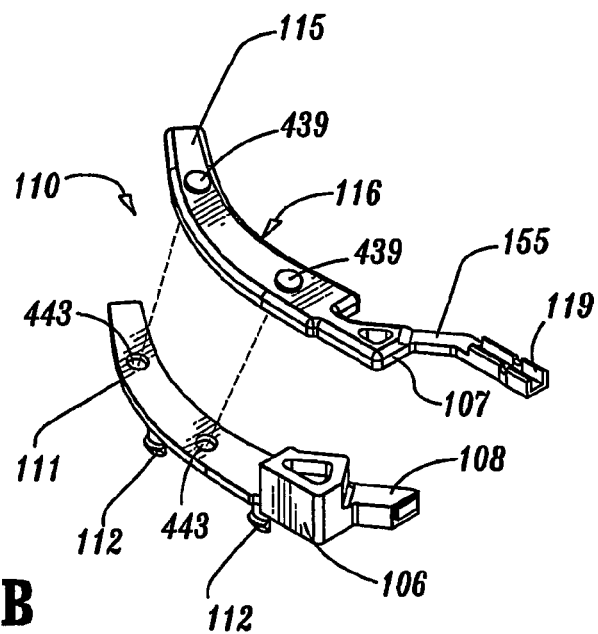
Figure 15C:
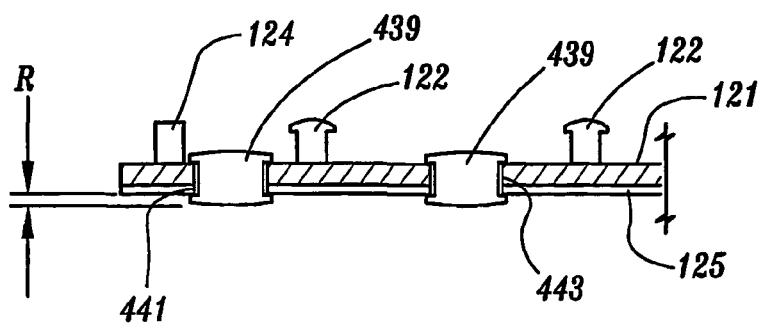

In another embodiment, the stop members may be dimensioned for selective and replaceable attachment to the jaw members depending upon a particular purpose. For example and as best shown in FIGS. 15A–15C, the stop members may be dimensioned as plugs 439 which selectively attach to the inner facing surfaces 115 and 125 of the jaw members through a series of apertures 441 and 443 defined through the inner surfaces 115, 125 and insulators 116, 126, respectively. The gap plugs 439 are preferably designed for snap-fit engagement through the apertures 441 and 443 of at least one of the jaw members, e.g., 120, and are dimensioned to protrude a distance "R" from the inner surfaces 125 thereof (FIG. 15C). As can be appreciated, the gap plugs 439 create minimum gap distance "G" (FIG. 8) between opposing inner facing surfaces 115 and 125 when the jaw members 110 and 120 cooperate to grasp tissue therebetween.

It is envisioned that a user may selectively engage one or more gap plugs 439 as needed to create a desired gap distance between the jaw members 110 and 120 during manipulation and/or sealing. As can be appreciated, the overall gap distance "G" is easily and selectively variable through substitution/replacement of a particularly-sized gap plug.

Preferably, the stop members 139, 239, 339 and/or 439 are made from an insulative material, e.g., parylene, nylon and/or ceramic and are dimensioned to limit opposing movement of the jaw members 110 and 120 to within a specified gap range. It is envisioned that the stop members 139, 239, 339 and/or 439 may be disposed one or both of the jaw members 110 and 120 depending upon a particular purpose or to achieve a particular result. Preferably, the stop members 139, 239, 339 and/or 439 may be configured in any known geometric or polynomial configuration, e.g., triangular, rectilinear, circular, ovoid, scalloped, etc., depending upon a particular purpose. Moreover, it is contemplated that any combination of different stop members 139, 239, 339 and/or 439 may be assembled along the sealing surfaces 115 and 125 to achieve a desired gap distance. Preferably, the non-conductive stop members 139, 239, 339 and/or 439 are molded onto the jaw members 110 and 120 (e.g., overmolding, injection molding, etc.), stamped onto the jaw members 110 and 120 or deposited (e.g., deposition) onto the jaw members 110 and 120. The stop members 139, 239, 339 and/or 439 may also be slideably attached to the jaw members and/or attached to the electrically conductive surfaces 115 and 125 in a snap-fit manner.

Other techniques for attaching the stop members 139, 239, 339 and/or 439 are also contemplated. For example, one technique involves thermally spraying a ceramic material onto the surface of the jaw member 110 and 120 to form the stop members 139, 239, 339 and/or 439. Several thermal spraying techniques are contemplated which involve depositing a broad range of heat resistant and insulative materials on the electrically conductive surfaces 115 and 125 to create stop members 139, 239, 339 and/or 439, e.g., High velocity Oxy-fuel deposition, plasma deposition, etc.

From the foregoing and with reference to the various figure drawings, those skilled in the art will appreciate that certain modifications can also be made to the present disclosure without departing from the scope of the present disclosure. For example, although it is preferable that electrodes 110 and 120 meet in parallel opposition, and, therefore, meet on the same plane, in some cases it may be preferable to slightly bias the electrodes 110 and 120 to meet each other at a distal end such that additional closure force on the handles 16 and 18 is required to deflect the electrodes in the same plane.

Although it is preferable to vertically align electrodes 110 and 120, in some cases it may be preferable to offset the opposing electrodes 110 and 120 relative to one another either longitudinally or transversally to suit a particular purpose.

Although it is preferable that the electrode assembly 21 include housing 71 and cover plate 80 to engage mechanical forceps 20 therebetween, in some cases it may be preferable to manufacture the disposable electrode assembly 21 such that only one piece, e.g., housing 71 is required to engage mechanical forceps 20.

While only one embodiment of the disclosure has been described, it is not intended that the disclosure be limited thereto, as it is intended that the disclosure be as broad in scope as the art will allow and that the specification be read likewise. Therefore, the above description should not be construed as limiting, but merely as exemplifications of a preferred embodiment. Those skilled in the art will envision other modifications within the scope and spirit of the claims appended hereto.

What is claimed is:

1. A removable electrode assembly for use with a forceps having opposing end effectors and a handle for effecting relative movement of the end effectors with respect to one another, the electrode assembly comprising:
   a cover plate having at least one portion which removably engages at least a portion of the forceps;
   an electrode housing having at least one portion which removably engages at least a portion of the forceps;
   a pair of electrodes attachable to a distal end of the housing, the electrodes being removably engageable with the end effectors of the forceps such that the electrodes are disposed in opposing relation to one another; and at least one stop member for controlling the distance between the opposing electrodes, the stop member being selectively engageable with the electrodes.

2. A removable electrode assembly according to claim 1 wherein each of the electrodes includes an electrically conductive sealing surface and an insulating substrate and the stop member is removably attached to the insulating substrate.

3. A removable electrode assembly according to claim 2 wherein the insulating substrate of each of the electrodes includes at least one mechanical interface which engages a complimentary mechanical interface disposed on the corresponding end effector of the forceps.

4. A removable electrode assembly according to claim 3 wherein the mechanical interface of at least one of the substrates includes at least one detent and the mechanical interface of the corresponding end effector includes at least one complimentary key-like socket for slideably and securely receiving the detent.

5. A removable electrode assembly according to claim 1 wherein the stop member is attached to at least one of the electrodes by thermal spraying.

6. A removable electrode assembly according to claim 1 wherein the stop member protrudes about 0.001 inches to about 0.005 inches from an inner facing surface of at least one of the end effectors.

7. A removable electrode assembly according to claim 1 wherein the stop member protrudes about 0.002 inches to about 0.003 inches from an inner facing surface of at least one of the end effectors.

8. A removable electrode assembly for use with a forceps having opposing end effectors and a handle for effecting relative movement of the end effectors with respect to one another, the electrode assembly comprising:

a cover plate having at least one portion which removably engages at least a portion of the forceps;

an electrode housing having at least one portion which removably engages at least a portion of the forceps;

a pair of electrodes attachable to a distal end of the housing, the electrodes being removably engageable with the end effectors of the forceps such that the electrodes are disposed in opposing relation to one another, each of the electrodes including an electrically conductive sealing surface and an insulating substrate; and at least one stop member for controlling the distance between the opposing electrodes, the stop member being selectively engageable with the electrodes, the stop member being removably attached to the insulating substrate.

9. A removable electrode assembly according to claim 8 wherein the mechanical interface of at least one of the substrates includes at least one detent and the mechanical interface of the corresponding end effector includes at least one complimentary key-like socket for slideably and securely receiving the detent.

10. A removable electrode assembly according to claim 8 wherein the stop member protrudes about 0.001 inches to about 0.005 inches from an inner facing surface of at least one of the end effectors.

11. A removable electrode assembly according to claim 8 wherein the stop member protrudes about 0.002 inches to about 0.003 inches from an inner facing surface of at least one of the end effectors.

* * * * *